US010563247B2

(12) United States Patent
Mao et al.

(10) Patent No.: US 10,563,247 B2
(45) Date of Patent: Feb. 18, 2020

(54) SINGLE-MOLECULE MECHANOANALYTICAL DNA DEVICE FOR ULTRASENSITIVE SENSING OF ANALYTES

(71) Applicant: KENT STATE UNIVERSITY, Kent, OH (US)

(72) Inventors: Hanbin Mao, Kent, OH (US); Shankar Mandal, Kent, OH (US)

(73) Assignee: KENT STATE UNIVERSITY, Kent, OH (US)

( * ) Notice: Subject to any disclaimer, the term of this patent is extended or adjusted under 35 U.S.C. 154(b) by 140 days.

(21) Appl. No.: 15/492,481

(22) Filed: Apr. 20, 2017

(65) Prior Publication Data
US 2017/0314066 A1 Nov. 2, 2017

Related U.S. Application Data

(60) Provisional application No. 62/328,067, filed on Apr. 27, 2016.

(51) Int. Cl.
| | | |
|---|---|---|
| C12Q 1/68 | (2018.01) | |
| C07H 21/00 | (2006.01) | |
| C12Q 1/6816 | (2018.01) | |
| C12Q 1/6804 | (2018.01) | |

(52) U.S. Cl.
CPC ........... *C12Q 1/6816* (2013.01); *C12Q 1/68* (2013.01); *C12Q 1/6804* (2013.01)

(58) Field of Classification Search
CPC ........ C12Q 1/00; C12Q 1/68; G01N 33/5302; C07H 21/00
See application file for complete search history.

(56) References Cited

U.S. PATENT DOCUMENTS

| | | | | |
|---|---|---|---|---|
| 5,424,413 A * | 6/1995 | Hogan | ................ | C12N 15/1068 435/6.1 |
| 2002/0197651 A1* | 12/2002 | Ward | ................... | G01N 33/582 435/7.1 |
| 2004/0078219 A1* | 4/2004 | Kaylor | ................ | G06F 19/3418 705/2 |
| 2007/0048759 A1* | 3/2007 | Luo | ...................... | C12Q 1/6816 435/6.19 |
| 2007/0117109 A1* | 5/2007 | Rothemund | ............ | C12P 19/34 435/6.12 |
| 2010/0099076 A1* | 4/2010 | Mao | ................. | G01N 33/543 13 435/5 |
| 2013/0005049 A1* | 1/2013 | Mao | ..................... | G01N 33/542 436/501 |
| 2014/0287424 A1* | 9/2014 | Cho | ......................... | C12Q 1/04 435/6.15 |
| 2017/0314066 A1* | 11/2017 | Mao | ........................ | C12Q 1/68 |

OTHER PUBLICATIONS

Ono et al., Highly Selective Oligonucleotide-Based Sensor for Mercury(ii) in Aqueous Solutions. Agnew. Chem. 116 : 4400 (Year: 2004).*
Chen et al., A New Aptameric Biosensor for Cocaine Based on Surface-Enhanced Raman Scattering Spectroscopy. Chemistry a European Journal 14 :8374 (Year: 2008).*
Fodey et al., Development of an Optical Biosensor Based Immunoassay to Screen Infant Formula Milk Samples for Adulteration with Melamine. Analytical Chemistry 83 : 5012 (Year: 2011).*
Haes et al., Detection of a Biomarker for Alzheimer's Disease from Synthetic and Clinical Samples Using a Nanoscale Optical Biosensor. JACS 127 :2264 (Year: 2005).*
Ivnitski et al., Biosensors for detection of pathogenic bacteria. Biosensors & Bioelectronics 14 : 599 (Year: 1999).*
Koirala et al.,—. Single-Molecule Mechanochemical Sensing Using DNA Origami Nanostructures. Agnew. Chem. Int. Ed. 53 :8137 (Year: 2014).*
Li et al. Silver-Ion-Mediated DNAzyme Switch for the Ultrasensitive and Selective Colorimetric Detection of Aqueous Ag+and Cysteine. Chemistry a European Journal 15 :3347 (Year: 2009).*
Liao et al., Use of Electrochemical DNA Biosensors for Rapid Molecular Identification of Uropathogens in Clinical Urine Specimens. J. of Clinical Microbiology 44 (2) : 561 (Year: 2006).*
Liu and Lu, A Colorimetric Lead Biosensor Using DNAzyme-Directed Assembly of Gold Nanoparticles. JACS 125 : 6642 (Year: 2003).*
Liu et al. Monoclonal Antibodies Directed Against the Outer Membrane Protein of *Bordetella avium*. Monoclonal Antibodies in Immunodiagnosis and Immunotherapy 32 (4) : 295 (Year: 2013).*
Support Information for Mandal et al. A Molecular Tuning Fork in Single-Molecule Mechanochemical Sensing. Agnew. Chem. Int. Ed. 54 : 7607 (Year: 2015).*
Song et al., Aptamer-based biosensors. Trends in Analytical Chemistry 27 (2) :108 (Year: 2008).*
Spangenberg et al., Highly sensitive, operationally simple, cost/time effective detection of the mycolactones from the human pathogen *Mycobacterium ulcerans*. Chem. Commun. 46 : 1410 (Year: 2010).*
Wang et al., Optical ATP Biosensor for Extracellular ATP Measurement. Biosensors & Bioelectronics 43 :355 (Year: 2013).*
Wu et al., Ultrasensitive aptamer biosensor for arsenic(III) detection in aqueous solution based on surfactant-induced aggregation of gold nanoparticles. Analyst 137 :4171 (Year: 2012).*
Cammann; Bio-sensors based on ion-selective electrodes; Anal. Chem., 1977, pp. 1-9, vol. 287.

(Continued)

*Primary Examiner* — Ethan C Whisenant
(74) *Attorney, Agent, or Firm* — Hudak, Shunk & Farine Co. LPA

(57) ABSTRACT

A single-molecule mechanoanalytical real-time sensing device (SMART) comprising a molecular trawl and a DNA stem-loop structure that serves as a molecular dipstick, said trawl and said DNA stem-loop structure anchored by handles to two optically-trapped bead templates; said molecular trawl comprising multiple analyte recognition elements that exist in each of two separate DNA (pair) strands that act as two pincers, said pincers each having a nucleobase capable of catching an analyte in a media; said DNA stem-loop structure comprising a plurality of nucleotides in said loop and multiple base pairs in said stem; and wherein said DNA stem-loop is located generally opposite to said molecular trawl that is capable of reporting an amount of bound analyte target via mechanochemical transient events.

20 Claims, 8 Drawing Sheets
(8 of 8 Drawing Sheet(s) Filed in Color)

Specification includes a Sequence Listing.

(56) References Cited

OTHER PUBLICATIONS

Thevenot, Electrochemical biosensors: recommended definitions and classification, Biosens. Bioelectron, 2001, pp. 121-131, vol. 16(1-2).

Lequin, Enzyme immunoassay (EIA)/enzyme-linked immunosorbent assay (ELISA). Clin. Chem. 2005, pp. 2415-2418, vol. 51.

Shrestha, Mechanochemical Sensing: A Biomimetic Sensing Strategy, ChemPhysChem, 2015, pp. 1829-1837, vol. 16.

Tchounwou, Review: Environmental exposure to mercury and its toxicopathologic implications for public health, Environ. Toxicol, 2003, pp. 149-175, vol. 18.

Miyake, MercuryII-Mediated Formation of Thymine-Hg(II)-Thymine Base Pairs in DNA Duplexes. J. Am. Chem. Soc., 2006, pp. 2172-2173, vol. 128.

Cizdziel, Determination of total mercury in human hair and animal fur by combustion atomic absorption spectrometry, Talanta, 2004, pp. 918-921, vol. 64.

Suvarapu, Recent Developments in the Speciation and Determination of Mercury Using Various Analytical Techniques, J. Anal. Methods Chem., 2015, pp. 372459, vol. 5.

U.S. EPA. National Primary Drinking Water Regulations. US EPA, 2009. http://water.epa.gov/drink/contaminants/index.cfm#List.

Jenner, B.J. ICP-MS—A powerful tool for high-precision trace-element analysis in Earth sciences: Evidence from analysis of selected U.S.G.S. reference samples. Chem. Geology, 1990, pp. 133-148, vol. 83.

Li, Sequential cloud point extraction for the speciation of mercury in seafood by inductively coupled plasma optical emission spectrometry. Spectrochim. Acta B, 2007, pp. 1153-1160, vol. 62.

Oliveira, Sample preparation for atomic spectroscopy: evolution and future trends. J. Braz.Chem. Soc., 2003, pp. 174-182, vol. 14.

Kong, An ultrasensitive electrochemical "turn-on" label-free biosensor for Hg2+ with AuNP-functionalized reporter DNA as a signal amplifier, Chem. Commun., 2009, pp. 5633-5635.

Yang, Multisignaling Optical-Electrochemical Sensor for Hg2+ Based on a Rhodamine Derivative with a Ferrocene Unit, Org. Lett, 2007, pp. 4729-4732, vol. 9.

Jiang, Resonance Scattering Spectral Detection of Trace Hg2+ Using Aptamer-Modified Nanogold as Probe and Nanocatalyst, Anal. Chem., 2009, pp. 5439-5445, vol. 81.

Nolan, Selective Hg(II) Detection in Aqueous Solution with Thiol Derivatized Fluoresceins, Inorg. chem., 2006, pp. 2742-2749, vol. 45.

Yang, A Rhodamine-Based Fluorescent and Colorimetric Chemodosimeter for the Rapid Detection of Hg2+ Ions in Aqueous Media, J. Am. Chem. Soc., 2005, pp. 16760-16761, vol. 127.

Liu, Biosensing by Tandem Reactions of Structure Switching, Nucleolytic Digestion, and DNA Amplification of a DNA Assembly, Angew. Chem. Int., 2015, pp. 9637-9641, Ed. 54.

Zhang, Predicting detection limits of enzyme-linked immunosorbent assay (ELISA) and bioanalytical techniques in general, 2014, pp. 439-445, Analyst 139.

Mandal, A Molecular Tuning Fork in Single-Molecule Mechanochemical Sensing, Angew. Chem. Int., 2015, pp. 7607-7611, Ed. 54.

Woodside, Nanomechanical measurements of the sequence-dependent folding landscapes of single nucleic acid hairpins, 2006, Proc. Natl. Acad. Sci., USA. 2006, pp. 6190-6195, vol. 103.

Torigoe, Hg(II) ion specifically binds with T:T mismatched base pair in duplex DNA, 2010, Chem. Eur. J., pp. 13218-13225, vol. 16.

Mammen, Polyvalent interactions in biological systems: implications for design and use of multivalent ligands and inhibitors, Angew. Chem. Int. Ed., 1998, pp. 2754-2794, vol. 37.

Koirala, Single-molecule mechanochemical sensing using DNA origami nanostructures, Angew. Chem. Int. Ed., 2014, pp. 8137-8141, vol. 53.

Mao, An integrated laser-tweezers instrument for microanalysis of individual protein aggregates, Sens. Actuators B, 2008, pp. 764-771, vol. 129.

Baumann, Ionic effects on the elasticity of single DNA molecules, Proc. Natl. Acad. Sci., USA, 1997, pp. 6185-6190, vol. 94.

Yu, Non-B DNA structures show diverse conformations and complex transition kinetics comparable to RNA or proteins—A perspective from mechanical unfolding and refolding experiments, Chem. Rec., 2013, pp. 102-116, vol. 13.

Dhakal, Structural and mechanical properties of individual human telomeric G-quadruplexes in molecularly crowded solutions, Nucleic Acids Res, 2013, pp. 3915-3923, vol. 41).

Mills, Flexibility of single-stranded DNA: use of gapped duplex helices to determine the persistence lengths of poly (dT) and poly(dA), J. Mol. Biol., 1999, pp. 245-257, vol. 285.

Mandal, Mechanochemical Sensing of Single and Few Hg(II) Ions Using Polyvalent Principles, Anal. Chem., 2016, pp. 9479-9485, vol. 88.

* cited by examiner

Single-molecule MechanoAnalytical Real Time Sensing (SMARTS)

FIG. 2A Different SMARTS devices
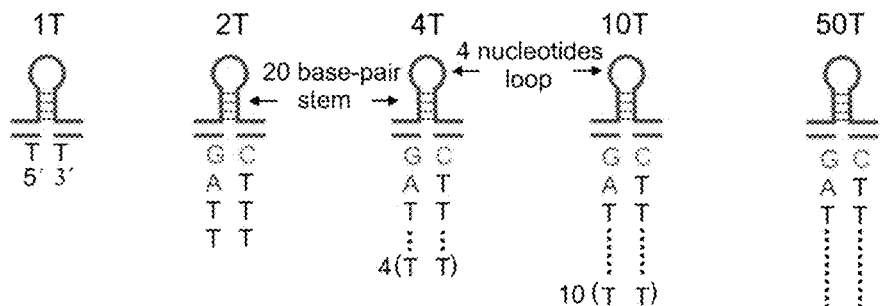
FIG. 2B  The 10T probe
FIG. 2C
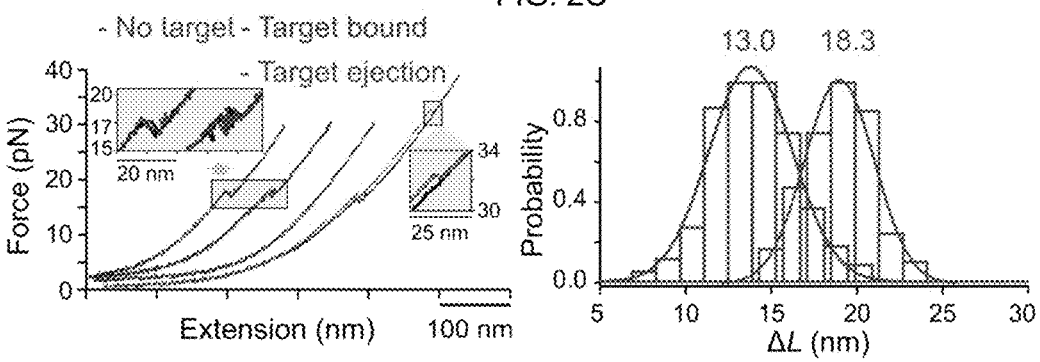
FIG. 2D
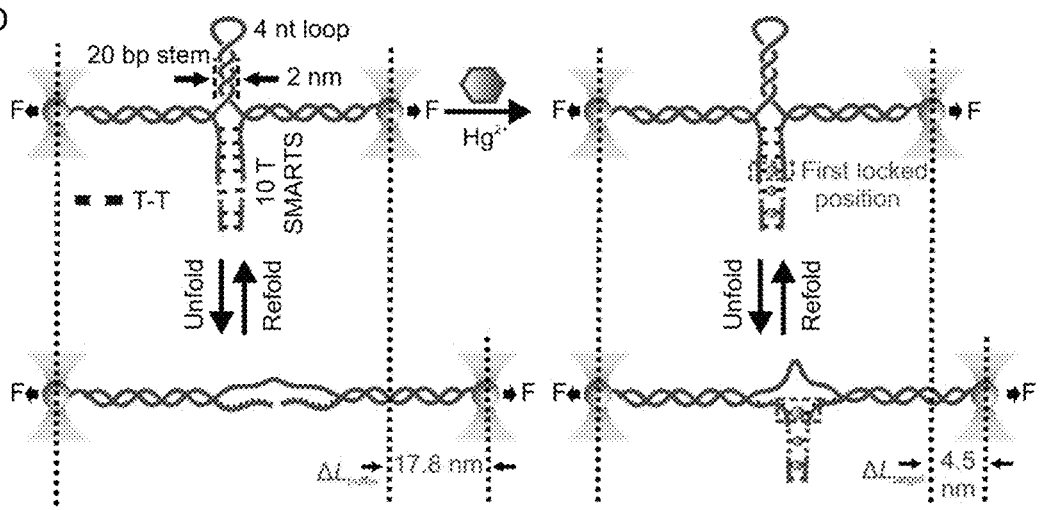
FIG. 2E
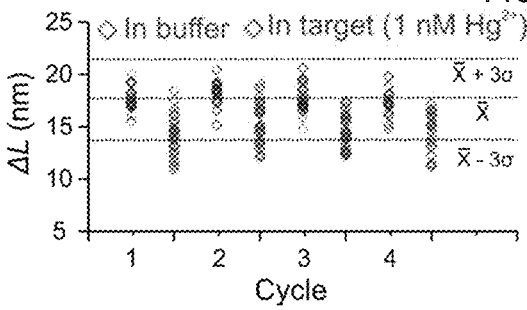
FIG. 2F Limit Of Detection (LOD)
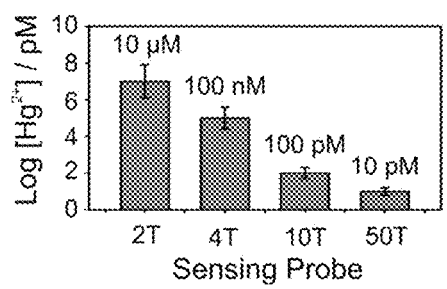

FIG. 3A  2T sensing probe
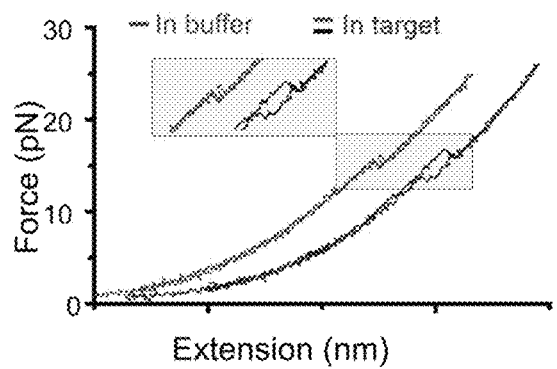
FIG. 3B  4T sensing probe
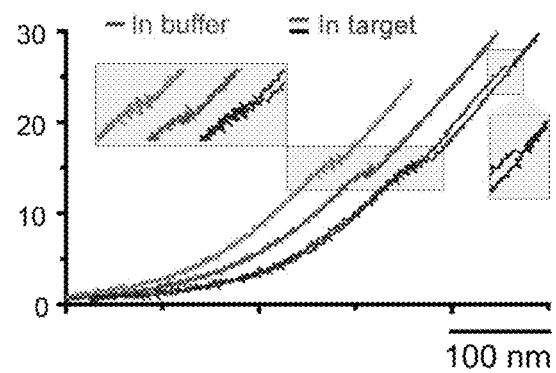
FIG. 3C  10 T sensing probe in buffer (F1/2 = 17.5 pN)
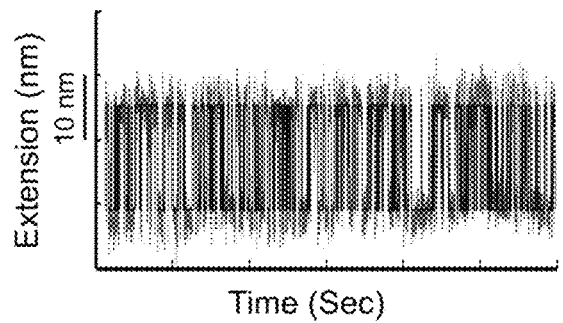
FIG. 3D  10 T sensing probe in target (F1/2 = 17.5 pN)
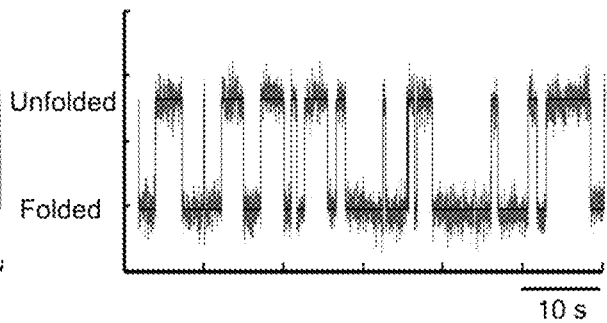

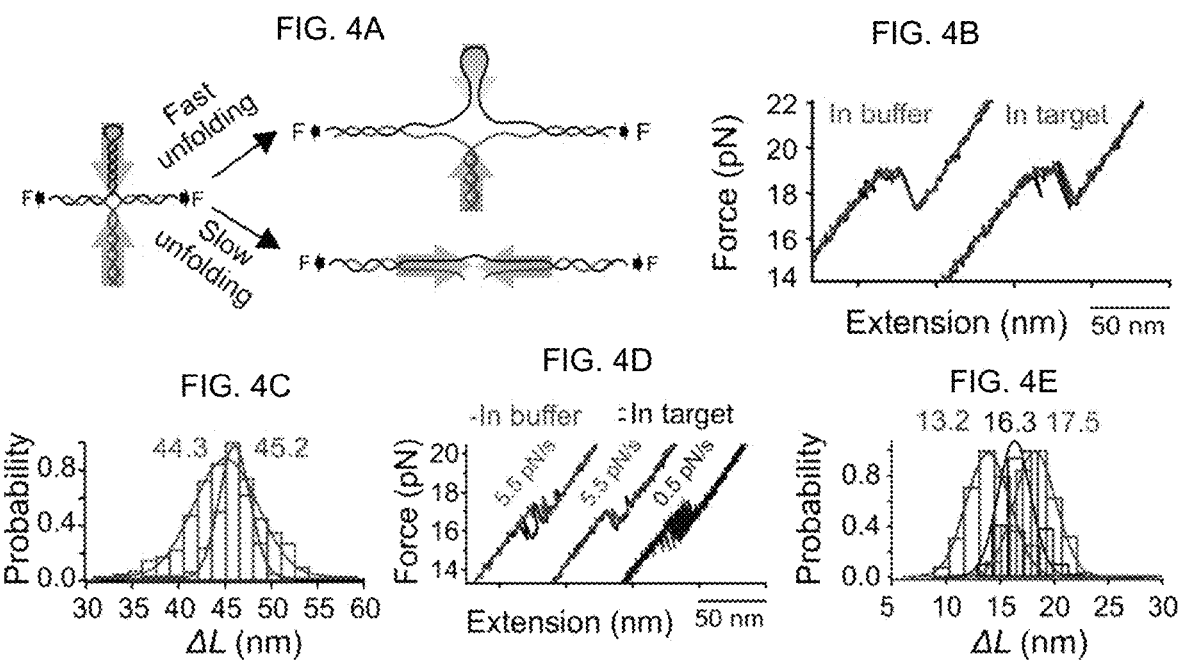

FIG. 7A Sensing probe 1T, 2T, 4T, 10T and 50T
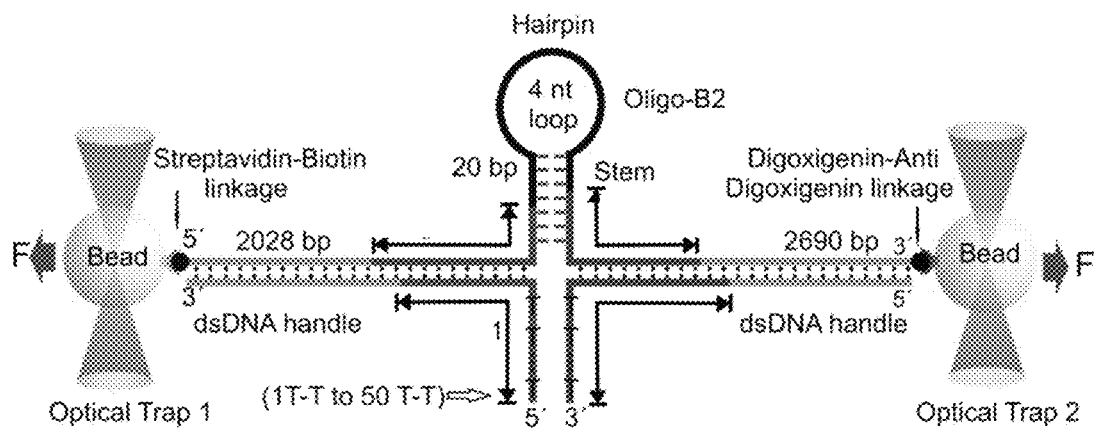
FIG. 7B Sensing probe 50T*
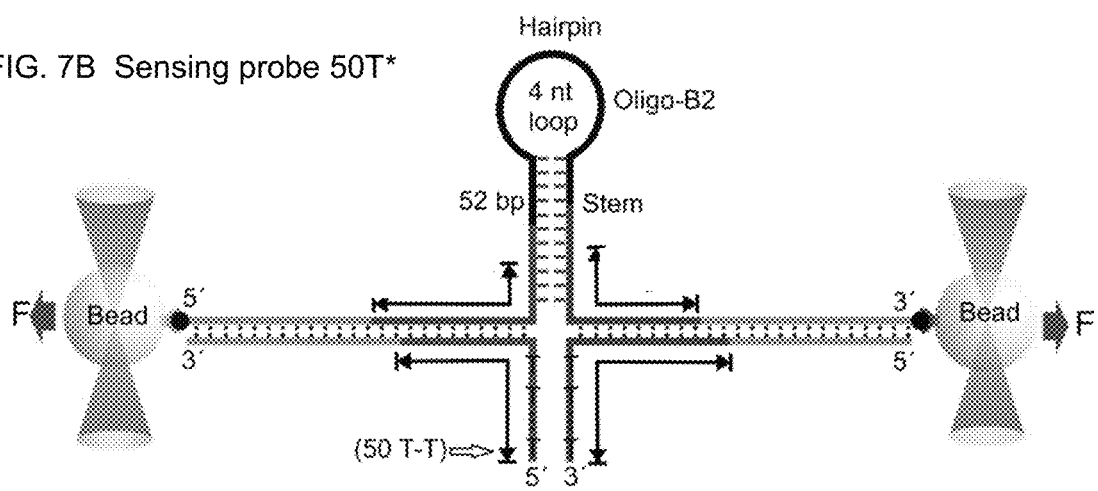
FIG. 7C Sensing probe 50T**
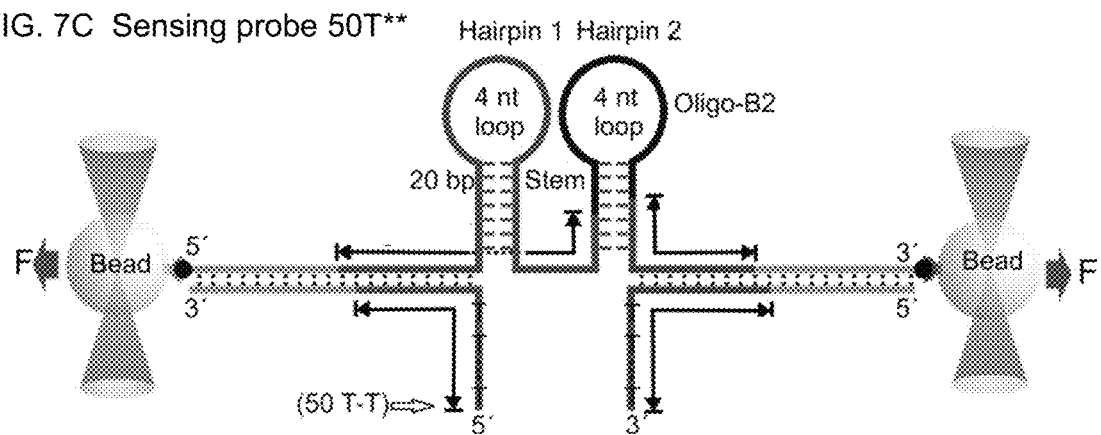

SINGLE-MOLECULE MECHANOANALYTICAL DNA DEVICE FOR ULTRASENSITIVE SENSING OF ANALYTES

FIELD OF THE INVENTION

Two basic units in conventional biosensors, molecular recognition and signal transduction, are often interconnected by amplification steps that set the detection sensitivity. Extra amplification steps, however, increase the complexity of a device and raise the uncertainty in the sensing. The present invention relates to a single-molecule mechanoanalytical real-time sensing devices (SMARTS) that exploit mechanochemical principles to avoid amplification steps. As a proof-of-concept, we used SMARTS to detect $Hg^{2+}$ ions. To achieve the utmost detection limit of single molecules, we used individual DNA templates to recognize $Hg^{2+}$ ions through thymine-$Hg^{2+}$-thymine (T-$Hg^{2+}$-T) interactions. To reduce background noise, each SMARTS device was anchored to two beads levitated by optical traps. To improve the detection limit for $Hg^{2+}$ ions, we introduced a new mechanism, molecular trawling, in which multiple T-T pairs are coordinated to increase the affinity for $Hg^{2+}$ ions. To effectively report T-$Hg^{2+}$-T formation, we constructed molecular dipsticks made of DNA hairpins. At certain force, hairpin dipsticks became unzipped until stable T-$Hg^{2+}$-T complexes were encountered. Owing to these innovations, we achieved an unprecedented 1 fM (femtomolar) ($2.0\times10^{-4}$ ppt (parts per trillion)) detection limit for $Hg^{2+}$ in 20 minutes in field samples treated by simple filtrations. The detection limit of the SMARTS demonstrated here is at least 2 order of magnitude lower compared to the most sensitive method described in literature. These new concepts and devices serve as critical components in mechanoanalytical chemistry, an emerging discipline that uses mechanochemical principles for chemical analyses of various targets ranging from small molecules such as ATP, cocaine, macromolecules (antibody), to whole cells.

Applications

1. The single-molecule mechanoanalytical real time sensing device (SMARTS) can be used for ultrasensitive and highly specific detection and quantification of $Hg^{2+}$ in water resources.
2. Mechanochemical studies of various targets such as antibodies, ATP, cocaine, nucleic acids and others in a biocompatible platform.

Advantages

1. Ultra-sensitive (1 fM (femtomolar)) detection of $Hg^{2+}$ within 20 minutes in field samples treated by simple filtrations. This detection limit is at least 2 orders of magnitude lower compared to the most sensitive existing method such as ICP-MS for $Hg^{2+}$ detection.
2. Simple, reliable and amplification free
3. Rapid analysis and low cost as sensing probe can be recycled many times.
4. Universal and different sensing probes (antigens, aptamers) can be easily integrated as signal reporting unit is separated from recognition unit.

BACKGROUND OF THE INVENTION

A conventional biosensor consists two major components, molecular recognition and signal transduction unit. While specificity is achieved through analyte recognition, the sensitivity is determined by the signal transducer that converts recognition events to measurable physiochemical signals[1-3]. In existing biosensors, analyte recognition and signal amplification are often decoupled spatiotemporally, such as ELISA (Enzyme Linked Immuno Sorbent Assay)[4] these two units require different sets of infrastructure. Although such a design avoids crosstalk between two basic components in a biosensor, the physical separation deteriorates temporal response of the sensors. Moreover, additional steps considerably increase complexity in the traditional sensing, which leads to additional errors that propagate through multiple stages and generate false positive or false negative results.

To address this issue, we have pioneered single-molecule mechanochemical sensing (SMMS)[5] in which mechanochemical coupling has been exploited to directly connect molecular recognition and signal transduction units. Mechanochemical coupling is often accompanied by a variation in mechanical properties, such as tension, in the macromolecule upon binding of a ligand. The change in the mechanical property can be monitored in real time using a laser tweezers instrument, accomplishing the sensing without extra infrastructure used in a separate signal transduction unit. Due to synchronizing issues, mechanochemical coupling is most conveniently observed in single-molecule templates. Although such templates offer the utmost sensitivity for individual molecules, which, in theory, can break the detection limit set by the binding affinity between an analyte and a recognition unit employed in ensemble-averaged sensors, the single-molecule platforms have limited space to accommodate expanded functionalities to improve the sensing. For instance, at extremely low analyte concentrations, binding events become so rare that waiting time is beyond experimental reach. To transform single-molecular sensing into highly competitive tools with expanded capabilities, here, we put forward a new concept, single-molecule mechanoanalytical real time sensing device (or SMARTS) that incorporates multiple functional units. We used this SMARTS device to detect $Hg^{2+}$ ions. Mercury contamination is a prevalent environmental concern as $Hg^{2+}$ is highly toxic by mutating genomic DNA through binding with a T-T mismatch pair in dsDNA[6,7]. Currently, $Hg^{2+}$ is determined by atomic absorption spectrometry (AAS) techniques with a detection limit at sub ppb ($1.0\times10^5$ fM) levels[8,9]. Such a level is close to the threshold of 2 ppb considered to be safe by EPA[10]. However, AAS and other $Hg^{2+}$ detection methods such as inductively coupled plasma-mass spectrometry (ICP-MS)[11], inductively coupled plasma-optical emission spectrometry (ICP-OES)[12], and cold vapor-atomic absorption spectrometry (CV-AAS)[13] often employ complex procedures that necessitate trained personnel to run the tests[14]. Recently, $Hg^{2+}$ has also been detected using electrochemical[15,16], optical[17], fluorescence[18,19], and colorimetric[19] detections. To the best of our knowledge, the detection limit of the SMARTS demonstrated here (1 fM in 20 minutes) is at least 2 orders of magnitude lower compared to the most sensitive method described in literature[9]. The SMARTS has a detection limit 9 orders of magnitude lower than the $K_d$, which represents at least 3 orders of magnitude improvement in sensitivity with respect to amplification based sensing[20] such as ELISA[21].

SUMMARY OF THE INVENTION

Sensitivity of conventional biosensors is ultimately limited by the dissociation constant ($K_d$) between analytes and probes. Although potent amplification schemes can be accommodated between analyte recognition and signal transduction in a sensor to improve the sensitivity 4-6 orders of magnitude below $K_d$, they compromise temporal resolution. Hereinafter, the use of the term DNA is meant to also include B-DNA that is found in nature. Here, we demonstrated single- and few-molecule sensing strategies that break the $K_d$ limit by 9 orders of magnitude for Hg detection in a real-time mechanochemical device. Analogous to trawl fishing, we accommodated multiple Hg recognition units (thymine (T)-thymine pairs) in a molecular trawl made of two separate polythymine DNA strands. However, the molecular trawl can be made of aptamers, which are DNA strands having different sequences to accommodate different targets. For example, DNA strands containing cytosine (C), guanine (G), adenine (A), and thymine (T) can make a binding pocket for ATP (adenine tri-phosphate) or other small molecular targets; polycytosine DNA strands can bind with $Ag^+$; and DNA strands labeled with specific antigens can specifically recognize antibodies. Numerous different types of two separate strands (pair) of DNA molecules can be utilized that contain the noted DNA strands containing (C) and (G), and/or (A) and (T) nucleotides. An important aspect of the present invention is that such types of DNA contain one or more analyte recognition elements as noted above as well as protein or nucleic acids. Generally, the number of nucleotides in each separate trawl strand, independently, is from about 2 to about 200, desirably from about 10 to about 100, and preferably from about 20 to about 50. Mechanical information (force/extension) was followed in a DNA hairpin dipstick (loop and stem) to measure the few $Hg^{2+}$ ions bound to the molecular trawl, which was levitated by two optically trapped particles. The particles were contained in the two optical beads, each of which receives a laser beam that sets or establishes the distance between the two end beads as shown in FIGS. 1 and 7. The structure of the optically-trapped beads are known to the art and to the literature and generally comprise glass, a polymer such as an acrylic, polyester, and the like, fused silica, boron nitride, or any combination thereof, or other transparent element. Preferably, the index of refraction of the bead material is greater than the index refraction of the media, for example water, aqueous buffer, and the like. The method of adding optically-trapped beads to handles is well known to the art and to the literature. These innovations allowed us to detect unprecedented 1 fM Hg ions in 20 minutes in field samples treated by simple filtrations. The detection limit of the mechanoanalytical device demonstrated here (1 fM) is at least 2 orders of magnitude lower than the most sensitive methods such as ICP-MS, ICP-OES, and CV-AAS for $Hg^{2+}$ detection. The SMARTS can have high versatility to detect a range of different analytes (small molecules such as ATP (adenine tri-phosphate), cocaine, melamine, antibodies[22], nucleic acids, various bacteria such as *mycobacterium ulcerans*, and *bordetella avium*, toxic metals (Pb, Ag, As), various diseases biomarkers such as HIV-1 protease, hepatitis C virus helicase and the like), simply by using different sensing probes.

A single-molecule mechanoanalytical real-time sensing device (SMART) comprising a molecular trawl and a DNA stem-loop structure that serves as a molecular dipstick, said trawl and said DNA stem-loop structure capable of being anchored by DNA handles to two optically-trapped beads; said molecular trawl comprising multiple analyte recognition elements that exist in each of two separate DNA strands that act as two pincers, said pincers each having an analyte recognition element capable of catching an analyte in a media; said DNA stem-loop structure comprising a plurality of nucleotides and multiple base pairs; and wherein said DNA stem-loop is located generally opposite to said molecular trawl that is capable of reporting an amount of bound analyte target via mechanochemical transient events.

A process for measuring very small amounts of an analyte, comprising the steps of: forming a SMART device, said SMART device comprising a molecular trawl and a DNA stem-loop structure that serves as a molecular dipstick, said trawl and said DNA stem-loop structure anchored by handles to two optically-trapped beads; said molecular trawl comprising multiple analyte recognition elements that exist in each of two separate DNA strands that act as two pincers, said pincers each having an analyte recognition element capable of catching an analyte in a media; said DNA stem-loop structure comprising a plurality of nucleotides and multiple base pairs; and wherein said DNA stem-loop is located generally opposite to said molecular trawl that is capable of reporting an amount of bound analyte target via mechanochemical transient events; and calculating the amount of analyte captured by said SMART device.

DESCRIPTION OF THE DRAWINGS

"The present patent application file contains at least 8 drawings executed in color. Copies of this patent or patent application publication with colored drawings will be provided by the Patent Office upon request and payment of the necessary fee".

FIG. 1 is a schematic of single-molecule mechanoanalytical real time sensing device (SMARTS) utilizing the concept of fishing trawl and oil dipstick.

FIG. 2 shows molecular trawling for $Hg^{2+}$ recognition. FIG. 2A shows a molecular trawling consisting 1T, 2T, 4T, 10T, and 50T (Thymine) in each of the two separate DNA strands acts as sensing probe. $Hg^{2+}$ binds with the template via the T-$Hg^{2+}$-T linkage. The same hairpin dipstick (a 20 base-pairs stem with 4 nucleotides loop) was used for each trawl. FIG. 2B shows a representative force-extension (F-X) curves of the 10T sensing probe in a 10 mM Tris buffer (pH 7.4, supplemented with 100 mM KCl and 5 mM EDTA, green), and in the same Tris buffer (without EDTA) with 1 nM $Hg^{2+}$ (red for $Hg^{2+}$ binding and blue for target ejection at higher force). Curves are offset in X axis for clarity. FIG. 2C shows $\Delta L$ histograms for the 10T SMARTS with (red) and without (green) 1 nM $Hg^{2+}$ in the Tris buffer. FIG. 2D shows a mechanism of $Hg^{2+}$ binding to the 10T SMARTS device. FIG. 2E shows a probe recycling and subsequent detection of the target by switching the 10T probe back and forth between the Tris buffer and the target (1 nM $Hg^{2+}$ in the Tris buffer without EDTA) channel in a microfluidic chamber. FIG. 2F shows a limit of detection (LOD) of $Hg^{2+}$ for different sensing probes. Error bars were calculated from the predicted LOD for 50% binding of the sensing probe.

FIG. 3 shows typical force-extension (F-X) curves and real time detection of $Hg^{2+}$ using different sensing probes in 10 mM Tris buffer (pH 7.4, supplemented with 100 mM KCl and 5 mM EDTA) and in $Hg^{2+}$ solution. FIG. 3A shows F-X curves of the 2T sensing probe in a Tris buffer showed reversible transition at 17.5 pN force (green). Binding of $Hg^{2+}$ at 100 μM concentration level formed a small hysteresis in the transition (blue). FIG. 3B shows F-X curves of the 4T sensing probe in Tris buffer (green) showed transition with reduced magnitude of transition in presence of $Hg^{2+}$ (100 nM). High force unfolding features indicating force induce breaking of T-$Hg^{2+}$-T bonds were observed (blue). Maximal mechanoescence of equally populated unfolded and folded states of the hairpin in 10 M Tris buffer (pH 7.4) FIG. 3C shows in 1 μM $Hg^{2+}$ and FIG. 3D shows under $F_{1/2}$=17.5 pN. The folding ($k_{on}$) and unfolding ($k_{off}$) rates reveal decreased values with 99% confidence level in the $Hg^{2+}$ binding ($k_{on}$=2.0±0.1 $s^{-1}$ and $k_{off}$=1.9±0.1 $s^{-1}$) with respect to those observed in the free buffer ($k_{on}$=2.7±0.2 $s^{-1}$ and $k_{off}$=2.6±0.2 $s^{-1}$);

FIG. 4 shows molecular dipsticks to report $Hg^{2+}$ binding. FIG. 4A shows a sensing mechanism of the 50T* SMARTS containing 50 T-T mismatch pairs as the target recognition unit and a 108-nt dipstick hairpin (a 52-bp stem and a 4-nt loop) to report the target binding. FIG. 4B shows a typical force-extension (F-X) curves for the 50T* SMARTS in a 10 mM Tris buffer (pH 7.4, supplemented with 100 mM KCl and 5 mM EDTA) (green) and in 1 μM $Hg^{2+}$ (red). FIG. 4C shows ΔL histograms for the 50T* SMARTS in the Tris buffer (green) and in 1 μM $Hg^{2+}$ (red). FIG. 4D shows representative F-X curves for the 10T SMARTS in the Tris buffer (green, pulling rate 5.5 pN/s) and 100 nM $Hg^{2+}$ with different loading rates (red and blue for 5.5 and 0.55 pN/s loading rates, respectively). FIG. 4E shows ΔL histograms for the 10T SMARTS in the Tris buffer (green, loading rate 5.5 pN/s) and in 100 nM $Hg^{2+}$ (red and blue for loading rates of 5.5 and 0.55 pN/s respectively). Curves in FIG. 4B and FIG. 4D are offset in the X-axis for clarity.

FIG. 5 shows construction of ultrasensitive mechanoanalytical device for $Hg^{2+}$ sensing.

FIG. 6 shows specificity and detection limit of the SMARTS devices.

FIG. 7 is a schematic of three specific DNA constructs that can be used in the single-molecule mechanoanalytical real time sensing devices (SMARTS) of the present invention. FIGS. 7A, 7B, and 7C show a general overall structure of the SMART sensing device of the present invention wherein the trawl is generally located beneath the loop and stem structure, i.e. vertically below, and horizontal handles that are utilized to connect both the loop-stem and trawl structure to optically-trapped bead. FIGS. 7A, 7B, and 7C graphically show the various elements of the SMARTS device of the present invention containing a hairpin or loop at the top of each schematic that is connected to two stems which in turn are connected to two separate handles. Also shown at the bottom of each schematic are two separate trawl strands that are also connected to two separate handles. Such connections or bonding are well known to the DNA art and are formed by standard or conventional molecular biology methods.

FIG. 8 is a schematic of the microfluidic sensing platform showing dimensions of the channels and the distance between the buffer and the target channels.

DETAILED DESCRIPTION OF THE INVENTION

Single-Molecule Mechanoanalytical Real Time Sensing (SMARTS) Device.

Figure 1A:
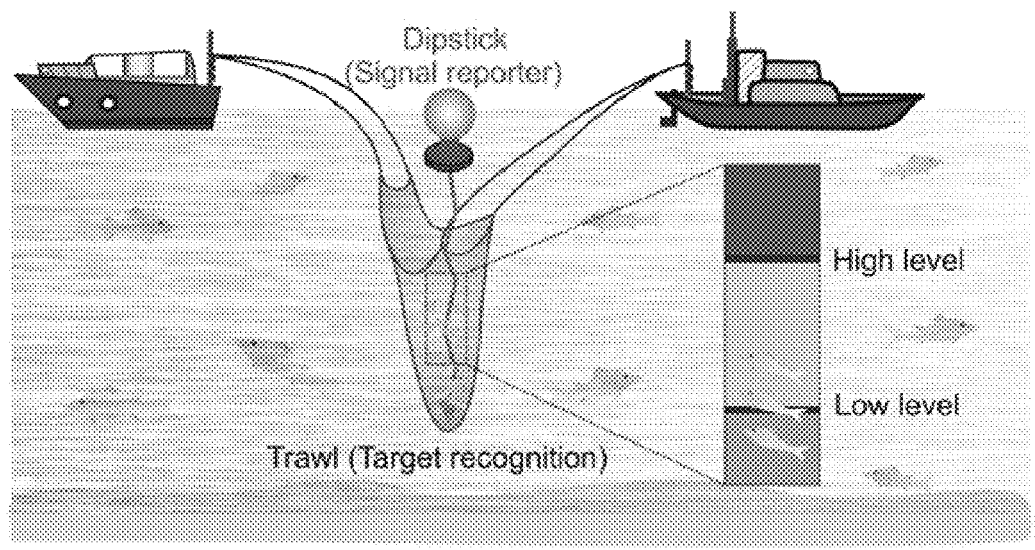
FIG. 1A shows a trawl net is anchored to two moving boats used to catch fish. Analogous to a dipstick to gauge the level of engine oil, a dipstick can report the amount of fish caught in the net.
Figure 1B:
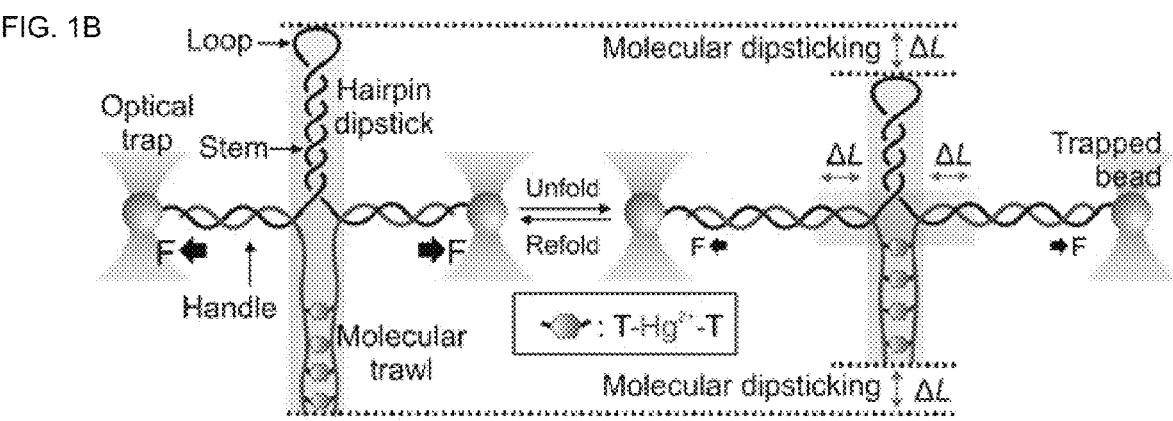
FIG. 1B shows a single-molecule mechanoanalytical device comprises molecular trawling and dipstick made of individual DNA molecules anchored to two optically trapped beads. Molecular trawl contains multiple recognition elements in each of two separate DNA strands (ssDNA) serving as two pincers. Catch of an analyte (green hexagon) requires two elements from the two pincers. A DNA hairpin acts as a molecular dipstick to report the amount of bound target via mechanochemical unfolding events. Target binding in the SMARTS leads to a reduced signal in the change-in-contour-length ($\Delta L$, see FIG. 2D for calculation).

The SMARTS device is inspired by the trawling mechanism in fishing and the dipstick concept to gauge the level of the material (oil in particular) inside a closed container (FIG. 1A). Using a trawl net anchored to two moving boats, trawling has been frequently employed in the fishing industry as well as in scientific surveys. The large surface of a trawl ensures efficient netting of desired products in ocean. In the first component of a SMARTS device, we will incorporate the trawling mechanism for sensing. We will use individual DNA molecules in two separate strands, having different sequences to accommodate different targets for example, polythymine DNA strands can bind with $Hg^{2+}$, DNA strands containing cytosine, guanine, adenine, and thymine can make a binding pocket for ATP or other small molecular targets. It is an important aspect of the present invention that with respect to the trawl, the two separate DNA strands have different sequences of generally G and C, and/or A and T, or combinations thereof. Examples of such few trawl sequences are set forth in Table 1. Thus, numerous different DNA sequences can be used in each of the two separate (pair) of trawl strands wherein each strand contains either the same or different sequence. DNA strands labeled with specific antigens can specifically recognize antibodies as templates which are anchored to two optically trapped beads via two long dsDNA handles. (FIG. 1B). The molecular trawl is made of multiple recognition elements in each of two separate ssDNA (single stranded DNA) strands serving as two pincers. For example the vertical pendant strands shown in FIG. 1B extend downwardly from the horizontal handles. The number of nucleotides in each strand is desirably the same as the number of nucleotides in the remaining (second) strand, but also can be different.

The handles are generally made of dsDNA (double stranded DNA), having from about 4,000 to about 8,000 nucleotides in each handle, desirably from about 4,000 to about 6,000, and preferably from about 4,000 to about 5,000 nucleotides. That is, about 2,000 to about 4,000, desirably from about 2,000 to about 3,000, and preferably from about 2,000 to about 2,500 based pairs (bp) are utilized. Generally a double stranded DNA is utilized because it is very stable and easy to prepare. Generally any type, sequence, etc., of dsDNA can be utilized as is known to the art and to the literature.

Catch of an analyte requires two elements from the two pincers. Instead of moving a trawl to catch fish using boats, here we keep the anchoring beads and therefore, molecular trawl, standstill, while forcing the solution to flow by. Quite often, the product of trawling is checked by visual inspection after a trawl is surfaced. At the level of individual molecules, such an inspection is not possible. Noticing dipsticks can check the level of materials (for example engine oil) in a container (FIG. 1A), our SMARTS device will employ molecular dipsticks to determine whether analytes were caught in the molecular trawl (FIG. 1B).

A DNA stem-loop structure (hairpin) has stem (double stranded) DNA strands containing cytosine, guanine, adenine, or thymine, or any combination thereof, and a loop (single stranded) DNA strand containing A, C, G or T, or any combination thereof. However, the DNA loop strands can be different from the DNA stem strands in any one SMART device, but they are compatible with each other. Thymine is preferred in the loop of a dipstick that is located opposite to the molecular trawl in the SMARTS. Generally the number of nucleotides in the loop (single stranded DNA) structure is from about 2 to about 20, desirably from about 2 to about 10, and preferably from 2 to about 6. The total number of complementary (double stranded) DNA base pairs in the stem is generally from about 8 to about 40 or 50, or 60, desirably from about 10 to about 25, and preferably from about 15 to about 20. When the hairpin is subject to ~15 pN exerted by optical tweezers, the stem-loop is unraveled, which is accompanied by the unzipping of the two pincers in the molecular trawl (See FIGS. 2, 4 and 5). The force to fold and unfold the stem-loop, i.e. RF also referred to as a hairpin, is generally from about 8 pN (piconewtons) to about 20 pN, desirably from about 15 pN to about 20 pN, and as noted, preferably from about 17.5 pN. The unzipping is halted when the dipstick and the trawl encounter a mechanical block composed of analytes and recognition units in the SMARTS. By comparing partially unzipped dipstick with that of fully unzipped dipstick, which occurs when the SMARTS device is not bound with ligand, the catch of analyte molecules can be revealed (FIG. 2D).

The design of molecular trawl can be rather versatile. Either protein or nucleic acids can be used in the SMARTS device to specifically recognize chemical analytes. Since DNA is more stable and more cost-effective than proteins, we chose individual B-DNA molecules as templates for SMARTS. The templates can be made of aptamers, which are DNA strands having different sequences to accommodate different targets. For example, polythymine DNA strands can bind $Hg^{2+}$, DNA strands containing cytosine, guanine, adenine, and thymine can make a binding pocket for ATP or other small molecular targets, DNA strands labeled with specific antigens can specifically recognize antibodies. Although specific aptamers can be used as recognition elements for various targets ranging from small molecules, macromolecules, to whole cells, for its simplicity and environmental significance, we used T-T mismatch pairs to recognize $Hg^{2+}$ ions through the T-$Hg^{2+}$-T complex as the thymine residues bind to the $Hg^{2+}$ through covalent nitrogen-Hg bonds.

Molecular Trawling in the SMARTS.

To evaluate the efficacy of the molecular trawls for $Hg^{2+}$ detection, we varied the number of thymines in each trawl while using the same molecular dipstick reporter with a 20-bp (base pairs)-stem and a 4-nt (nucleotide) loop (FIG. 2A). We started with a molecular trawl that contains one thymine in each ssDNA pincer. However, no binding of $Hg^{2+}$ was observed probably due to the weak affinity of the $Hg^{2+}$ in the single T-T pair. Switching the trawl to two or four adjacent thymines (2T and 4T sensing probe, FIG. 2A), respectively, in each pincer gave positive results in force-ramping experiments (FIGS. 3A & 3B) but showed negative results in force-clamp experiments. In force-clamp experiments the hairpin dipstick transits rapidly between folded and unfolded states at a constant force (or mechanoescence[22], FIG. 3C) without any $Hg^{2+}$ in the buffer). From the force-extension (F-X) curves collected during force-ramping experiments, the mechanoescence was also obvious by the reversible folding and unfolding events at 17.5 pN (FIG. 2B). Upon placing the 10TSMARTS in a microfluidic channel with 1 µM $Hg^{2+}$, the mechanoescence became significantly slower (FIG. 3D). Likewise, the F-X curves showed transitions with reduced change-in-contour length (ΔL) or without any feature (FIG. 2B). When we reduced the $Hg^{2+}$ concentration, it became more difficult to observe the change in mechanoescence due to the fact that during the folding-unfolding transitions, two pincers in the molecular trawl came closer only momentarily, which reduces the chance to catch $Hg^{2+}$ ions. Therefore, for reduced concentration, F-X detection mode was used in the sensing. In this mode, the ΔL was measured from the F-X curve each time a SMARTS device was mechanically stretched. Comparison of the ΔL values between the buffer channel and the target channel (1 nM) showed significantly smaller ΔL in the latter (FIG. 2C), confirming the catch of the $Hg^{2+}$ by the SMARTS in the target channel. In a preferred embodiment, the trawl has at least 2 adjacent thymines (2T) to about 200, desirably from about 10 to about 100, and preferably from about 20 to about 50 T in each strand.

At low analyte concentrations, however, not every F-X curve shows the evidence of catching $Hg^{2+}$ ions. This observation increases the uncertainty in the $Hg^{2+}$ sensing if rupture force histograms, which reflect average results, are compared. It is likely that with sufficiently low $Hg^{2+}$ concentration, the chance of $Hg^{2+}$ binding is so low that a ΔL histogram will not show a difference compared to that in the $Hg^{2+}$ free buffer. Therefore, we opted to determine the binding of $Hg^{2+}$ to the molecular trawl from individual F-X traces. To this end, first, we obtained more than 15 ΔL measurements in the buffer channel as a reference, from which average $ΔL_{average}$ and standard deviation (σ) was obtained. After the SMARTS was transported to the $Hg^{2+}$ channel, the binding of the $Hg^{2+}$ was defined by the threshold value of $ΔL_{average}$-3σ (FIG. 2E). Therefore, for observed ΔL less than this value, there is 99.5% chance $Hg^{2+}$ binds to the molecular trawl. The detection limit of $Hg^{2+}$ was set when there is no sign of $Hg^{2+}$ binding in 20 minutes. As shown in FIG. 2F, when we increased the number of thymines in molecular trawls, the detection limit reduces. For a 10T SMARTS, the detection limit was 100 pM (Picomolar). When a 50T SMARTS was used, the detection limit reduced to 10 pM (FIG. 2F). It is noteworthy that the SMARTS device can be transported back to the buffer channel that contains 5 mM EDTA to remove the $Hg^{2+}$ ions caught in the target channel (FIG. 2E). During experiments, more than 10 such probe recycling was performed without deterioration in the sensing capability of the 10T SMARTS.

Molecular Dipsticks in the SMARTS.

The hairpin dipstick we used for the 50T SMARTS device only contained 44 nucleotides (a 20-bp stem and a 4-nt loop). This dipstick may not be able to probe beyond 22 thymines in the molecular trawl, irrespective of the binding of $Hg^{2+}$ in this region. In the next step, we increased the length of the hairpin dipstick to 108 nucleotides (a 52-bp stem and a 4-nt loop) so that it can reach the bottom of the 50T* molecular trawl (FIG. 4A). Almost identical $\Delta L$ were obtained with or without $Hg^{2+}$ ions (FIGS. 4B and 4C), indicating the binding of $Hg^{2+}$ was not observed even at high concentration of 1 μM. Close inspection on the unfolding features in F-X curves (FIG. 4B) revealed a plateau force of ~15 pN during which hairpins started to unzip. Such a transition provided a longer time window in which bound $Hg^{2+}$ may become dissociated. To verify this, we performed force-ramping experiments on the 10T SMARTS with reduced loading rates (5.5 pN/s→0.55 pN/s) in 100 nM $Hg^{2+}$. As expected, the binding of $Hg^{2+}$ was not obvious (FIGS. 4D and 4E).

Figure 5A:
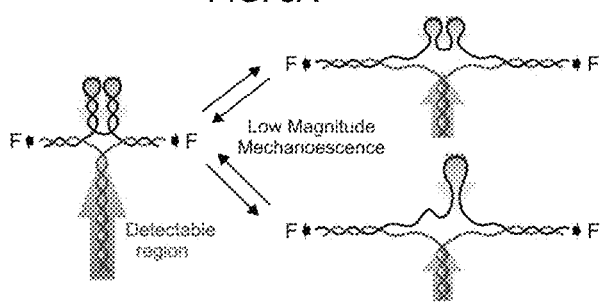
FIG. 5A shows a sensing mechanism of the 50T** SMARTS that contains 50 T-T mismatches as a molecular recognition unit and two 44-nt (a 20 bp stem and a 4 nt loop) dipstick hairpin reporters.
Figure 5B:
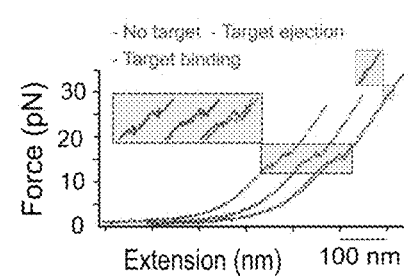
FIG. 5B shows representative F-X curves show two stochastic transition events corresponding to the two hairpins in the Tris buffer (green) and in 100 fM $Hg^{2+}$ target (red). The ejection of bound $Hg^{2+}$ was depicted in blue traces.
Figures 5C, 5D:
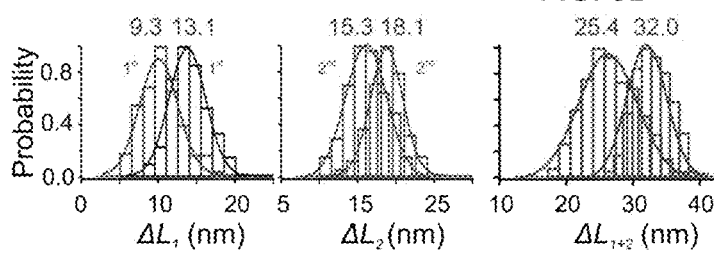
FIG. 5C shows ΔL histograms for the first (left panel) and the 2nd unfolding event (right) in the Tris buffer (green) and in 100 fM $Hg^{2+}$ (red).
FIG. 5D shows a cumulative ΔL histograms for the unfolding events of both hairpins in the Tris buffer (green) and in 100 fM $Hg^{2+}$ (red).
Figure 5E:
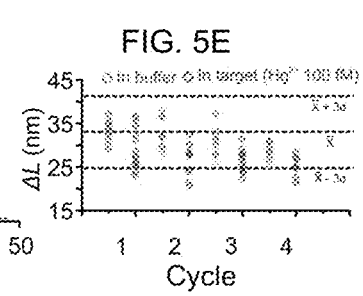
FIG. 5E shows a probe recycling and subsequent detection of target by switching the probe back and forth between the 10 mM Tris buffer (pH 7.4, supplemented with 100 mM KCl and 5 mM EDTA) and 100 fM $Hg^{2+}$ target in the Tris buffer without EDTA.

When hairpin becomes long, the unfolding transition of the hairpin is no longer cooperative[23]. Instead, the sawteeth unfolding features with a plateau force of ~15 pN could be observed, which leads to the unfolding of the $Hg^{2+}$ ions as discussed above. To serve as an effective reporter for analyte binding in the molecular trawling strategy, therefore, long hairpin dipsticks (about 52 total base pairs stems) are avoided. In an alternative approach, we designed two short hairpin dipsticks to gauge the binding of $Hg^{2+}$ (FIG. 5A). To effectively probe towards the bottom of the 50T trawl, the two hairpins had a total of 88 nucleotides with a 10-nt spacer (loop) in between. The binding of $Hg^{2+}$ anywhere in the 50 T-T pair trawling is expected to reduce the change-in-contour length as T-$Hg^{2+}$-T complex is strong enough to stop the unraveling of the two dipstick hairpins. The two hairpins unfold through two potential pathways: a sequential pathway in which one hairpin is unzipped totally before another starts to unravel; or a parallel pathway in which both hairpins are simultaneously unzipped. To differentiate these two cases, we separately plotted the $\Delta L$ histograms of the first and the second unfolding features. After comparing each histogram with or without $Hg^{2+}$ ions, we found parallel unfolding of both hairpins is more likely since each unfolding feature has a reduced $\Delta L$ value compared to that observed in pure buffer (FIGS. 5B and 5C). Due to this observation, we summed up $\Delta L$ values of the two features with or without $Hg^{2+}$ to determine the binding of $Hg^{2+}$ (FIG. 5D). It is obvious that in the $Hg^{2+}$ channel, there is reduced $\Delta L$ for an average transition with respect to those in the buffer channel. As discussed previously, however, in the channel with low $Hg^{2+}$ concentrations, it is not likely $Hg^{2+}$ is bound to the SMARTS each time a force ramping procedure was performed. Thus, comparison of $\Delta L$ histograms is not effective to determine the binding of $Hg^{2+}$ unambiguously. Again, we followed the $\Delta L$ for individual traces. Compared to the $\Delta L_{average}$ obtained in the buffer channel, if $\Delta L$ measured in the $Hg^{2+}$ channel is smaller than the 3 standard deviations of the $\Delta L_{average}$, the $Hg^{2+}$ is considered to be detected (FIG. 5E). With this algorithm, we determined the detection limit of 1 fM $Hg^{2+}$ in 20 minutes using the 50T** SMARTS device with 2 hairpin dipsticks (FIG. 5A). By moving back and forth between buffer and $Hg^{2+}$ channels, the sensor can be recycled for subsequent tasks without deterioration in the sensing capability (FIG. 5E).

Compared to the most sensitive methods of $Hg^{2+}$ sensing (~100 fM)[9], our approach presents at least about 2 orders of magnitude lower, desirably at least about 2.5, and preferably at least about 3 orders of magnitude lower in detection limit with a much simpler sample preparation. It is noteworthy that the detection limit can be further improved by using a longer time window preferably from 30 to about 45 min, with longer molecular trawling preferably from 100 to about 200 bp, or employing more trawls preferably from 4 to about 6 in the SMARTS. Given that the affinity ($K_d$) of $Hg^{2+}$ binding to a single T-T mismatch pair is in the μM ranges[24] it is surprising that femtomolar $Hg^{2+}$ concentration was detected here. This superb detection limit can be ascribed to three factors. First, the T-T mismatch pairs in the molecular trawling device are arranged in a polyvalent manner, which has a well-known entropic effect to increase the binding affinity[25]. Second, the multiple T-T pairs increased the effective local concentrations, increasing the $k_{on}$ for $Hg^{2+}$ binding. Finally, the 50T** SMARTS device can reach deeper into a solution, increasing the interaction area for $Hg^{2+}$ binding in a fixed time window.

Quantification of $Hg^{2+}$ in Field Samples.

Figure 6A:
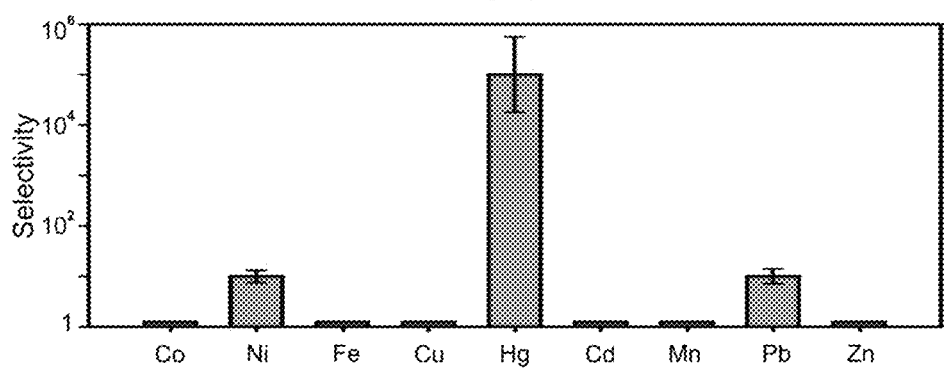
FIG. 6A shows a specificity test of $Hg^{2+}$ versus $Co^{2+}$, $Ni^{2+}$, $Fe^{2+}$, $Cu^{2+}$, $Cd^{2+}$, $Mn^{2+}$, $Pb^{2+}$, or $Zn^{2+}$ bindings to the 10T SMARTS.

Before testing field samples using these SMARTS devices, next, we evaluated its specificity. Using the similar approach as described in FIG. 2, we measured the detection limit for a range of ions, $Co^{2+}$, $Ni^{2+}$, $Fe^{2+}$, $Cu^{2+}$, $Hg^{2+}$, $Cd^{2+}$, $Mn^{2+}$, $Pb^{2+}$, and $Zn^{2+}$, using the 10T SMARTS construct. As shown in FIG. 6A, the selectivity for $Hg^{2+}$ is at least 4 orders of magnitude higher compared to the closest competitor, $Pb^{2+}$ and $Ni^{2+}$.

Figure 6B:
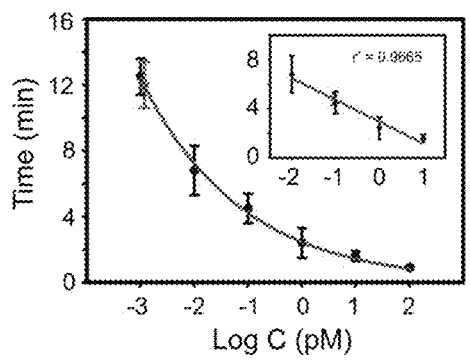
FIG. 6B shows a dynamic range (100 pM-1 fM) and linear range (100 pM-100 fM, with $r^2$=0.9665, see inset) for $Hg^{2+}$ binding to the 50T** SMARTS device. The cyanpoint depicts measurement of $Hg^{2+}$ from Lake Erie. The cyanpoint in the inset shows 40 times concentrated sample from Lake Erie.
Figure 6C:
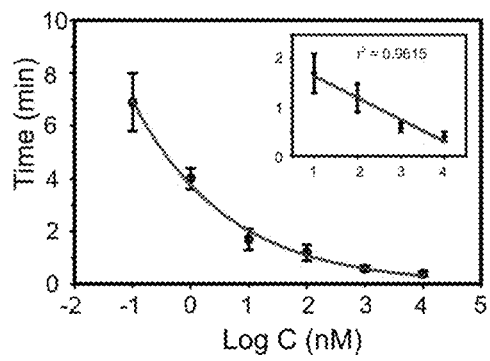
FIG. 6C shows a dynamic range (10 μM-100 pM) and linear range (10 μM-10 nM, with $r^2$=0.9615) of $Hg^{2+}$ binding to the 10T SMARTS device.

To quantify the concentration of $Hg^{2+}$ using the SMARTS device, we constructed calibration curves in which the observation time for the first binding event was plotted against the known $Hg^{2+}$ concentration. For the 50T** SMARTS with two hairpin dipsticks, we found the observation time decreased significantly with concentration in the dynamic range of 1 fM-100 pM (FIG. 6B). Depending on the concentration of an unknown, a linear relationship can be constructed inside this range (FIG. 6B inset). Above 100 pM, the observation time for the first binding was too short to accurately determine the concentration. However, using the 10T SMARTS, the dynamic range for high $Hg^{2+}$ concentrations (100 pM-10 pM) can be well established (FIG. 6C).

With the specificity and the quantification procedures firmly established, finally, we measured $Hg^{2+}$ concentration in Lake Erie. We first filtered Lake Erie water (Huntington Beach, Aug. 20, 2015) with a 200 nm-pore polystyrene filter, followed by direct injection into the microfluidic chamber (see Methods). By recording the time for the first binding events, we found 1.2±0.4 fM $Hg^{2+}$ (2.4×10$^{-4}$±0.8×10$^{-4}$ ppt) in the field sample using exponential fitting equation (FIG. 6B). Concentrating the same sample 40 times, the $Hg^{2+}$ in Lake Erie was determined to be 92±20 fM (equivalent to 2.3±0.5 fM $Hg^{2+}$ (4.6×10$^{-4}$±1.0×10$^{-4}$ ppt) in the pristine sample) using linear fitting equation (FIG. 6B, inset) These two values were close to each other to depict the reliability of the quantification method for the mechanoanalytical device.

In view of the above, the present invention relates to a SMART device for measuring very small amounts of an analyte. Various analytes have been set forth above as well as the important aspects of the device such as two optical trapped beads that position the SMART device, handles that are connected to the optical trapped beads and are connected to a loop and stem made of DNA strands, and also attached to two separate DNA strands that constitute a trawl. In one embodiment, the SMART device can be placed in an aqueous medium such as water and dragged through the same whereby the above-noted structure calculates the amount of an analyte in said fluid, or antipodally, where a fluid is forced through a stationary SMART device.

In summary, we have successfully demonstrated first-in-class single-molecule mechanoanalytical real time sensing (SMARTS) devices. With the incorporation of molecular trawls for $Hg^{2+}$ recognition and molecular dipsticks to report $Hg^{2+}$ binding, an unprecedented detection limit of 1 fM $Hg^{2+}$ ($2 \times 10^{-4}$ ppt) was achieved in 20 minutes, which is two orders of magnitude lower than the best $Hg^{2+}$ detection method reported.[9] This detection limit is nine orders of magnitude lower than the $K_d$, which represents an improvement of three orders of magnitude compared to amplification based biosensing methods[21]. The SMARTS can have high versatility to detect a range of different analytes, which include small molecules as well as proteins and nucleic acids. As an example, we were able to detect 100 pM antibody in serum within 30 minutes using antigens as the sensing probe[22]. However, the novel concept of mechanoanalytical devices described here provides a key contribution to the mechanoanalytical chemistry[26], a new field that uses mechanochemical principles for chemical analyses.

Material and Methods

The DNA construct for single-molecule mechanochemical sensing (SMMS)[5] was prepared by sandwiching a DNA hairpin between two dsDNA handles (2690 and 2028 bp). Opposite to the hairpin, poly-thymine anti-parallel DNA oligomers were introduced to serve as molecular recognition unit for $Hg^{2+}$ binding (FIG. 7).

The 2690 bp dsDNA handle was constructed by SacI (NEB) and EagI (NEB) digestions of a pEGFP plasmid (Clontech, Mountain View, Calif.). The handle was gel purified and subsequently labeled at the 3' end by digoxigenin (Dig) using 18 μM Dig-dUTP (Roche, Indianapolis, Ind.) and terminal transferase (Fermentas, Glen Burnie, Md.). The Dig-labeled 2690 handle was purified by ethanol precipitation. The biotin labeled 2028 bp dsDNA handle was prepared by PCR amplification using a pBR322 template (New England Biolab, NEB) and a 5' biotinylated primer 5'-GCATTAGGAAGCAGCCCAGTAGTA GG-3' (IDT, Coralville, Iowa). The PCR product was purified with PCR purification kit (Qiagen, Germantown, Md.) and subsequently digested with XbaI restriction enzyme (NEB). The digested 2028 bp handle was gel purified using a kit (Midsci, St. Louis, Mo.). To optimize the single-molecule mechanoanalytical device, DNA constructs with different sensing probes were synthesized and compared for their sensing capacities (see FIG. 7).

In general, to synthesize the 1TDNA construct, an oligonucleotide 5'CTAG TG CAT TAG GAAGCAGCC CAG AAA GGTGCA CC 3' (Oligo-B1) which contained a part of the hairpin stem (8 nts, underlined) was annealed with an oligonucleotide 5' T TTTCTGGGCTGCTTC CTA ATG CA 3' (Oligo-B5.1) at 97° C. for 5 min and slowly cooled to room temperature for 6 hours.

This fragment was ligated with the 2028 bp DNA handle by T4DNA ligase (NEB) and gel purified using a kit (Midsci, St. Louis, Mo.). On the other side of the DNA construct, oligonucleotides 5' GGACGGTGC ACC AAA AGCAAGACG TAG CCC AGCGCG 3' (Oligo-B3) containing another part of the hairpin stem (12 nts, underlined) was annealed with oligonucleotides, 5' GGCC CGCGCTGGG CTA CGT CTT GCTTTT T 3' (Oligo-B4.1). This fragment was ligated with the 2690 bp handle and gel purified. The final DNA construct was synthesized using T4DNA ligase (NEB) through three-piece ligation of the 2028 and 2690 bp DNA handles and an ssDNA fragment, 5' GTCCGG ACC CTGTTTTCAGGGT CC 3'(Oligo-B2), which contained a tetrathymine loop with underlined regions representing the complementary regions of the hairpin stem. Other DNA constructs such as 2T, 4T, 10T, 50T, 50T* and 50T** (FIG. 7) were synthesized using the similar strategy utilizing oligonucleotides listed in Table-1 for various trawls.

TABLE 1

Oligonucleotides used to synthesize different DNA constructs for SMARTS devices.

| Sensing probe | Oligo | Sequence (5'-3') | Length (nt) |
|---|---|---|---|
| 1T | B 1 | CTAG TG CAT TAG GAAGCAGCC CAG AAA GGTGCA CC | 35 |
|  | B 2 | GTCCGG ACC CTGTTTT CAG GGT CC | 24 |
|  | B 3 | GGACGGTGC ACC AAA AGCAAGACG TAG CCC AGCGCG | 36 |
|  | B 4.1 | GGCC CGCGCTGGG CTA CGT CTT GCTTTT T | 29 |
|  | B 5.1 | T TTTCTGGGCTGCTTC CTA ATG CA | 24 |
| 2 T | B 4.2 | GGCC CGCGCTGGG CTA CGT CTT GCT CTT T | 29 |
|  | B 5.2 | T TAG CTGGGCTGCTTC CTA ATG CA | 24 |
| 4 T | B 4.3 | GGCC CGCGCTGGG CTA CGT CTT GCT CTT TGTGTT C | 35 |
|  | B 5.3 | G TTC ACT TAG CTGGGCTGCTTC CTA ATG CA | 30 |
| 10 T | B 4.4 | GGCC CGCGCTGGG CTA CGT CTT GCT CT TTTTTTTTTT | 37 |
|  | B 5.4 | TTTTTTTTTT AG CTGGGCTGCTTC CTA ATG CA | 32 |
| 50 T | B 4.5 | GGCC CGCGCTGGG CTA CGT CTT GCT CT TTTTTTTTTTTTTTTTTTTTTTTTTTTTTTTTTTTTTTTTTTTTTTTTTT | 77 |
|  | B 5.5 | TTTTTTTTTTTTTTTTTTTTTTTTTTTTTTTTTTTTTTTTTTTTTTTTTT AG CTGGGCTGCTTC CTA ATG CA | 72 |
| 50 T* | B 1* | CTAG TG CAT TAG GAAGCAGCC CAG AAA GAT CAG TAG CGAGGCTGCAGTGTACGGAGGTCG GTG CAT C | 67 |
|  | B 2* | GTCCGG ACC CTGTTTT CAG GGT CC | 24 |
|  | B 3* | GGAC G ATG CAC CGACCT CCG TAC ACT GCAGCCTCG CTA CTG ATC AAA AGCAAGACG TAG CCC AG CGCG | 68 |

TABLE 1-continued

Oligonucleotides used to synthesize different
DNA constructs for SMARTS devices.

| Sensing probe | Oligo | Sequence (5'-3') | Length (nt) |
|---|---|---|---|
| 50 T** | B 1** | CTAG TG CAT TAG GAAGCAGCC CAG AAA GCAGGA ACA GGG AAT GCC CG TTTT CG GGC ATT CCC TGTTCCTGCCTAT CT AACTGGTGCA CC | 89 |
| | B 2** | GTCCGG ACC CTGTTTT CAG GGT CC | 24 |
| | B 3** | GGACGGTGC ACC AAA AGCAAGACG TAG CCC AGCGCG | 36 |

Figure 8A:
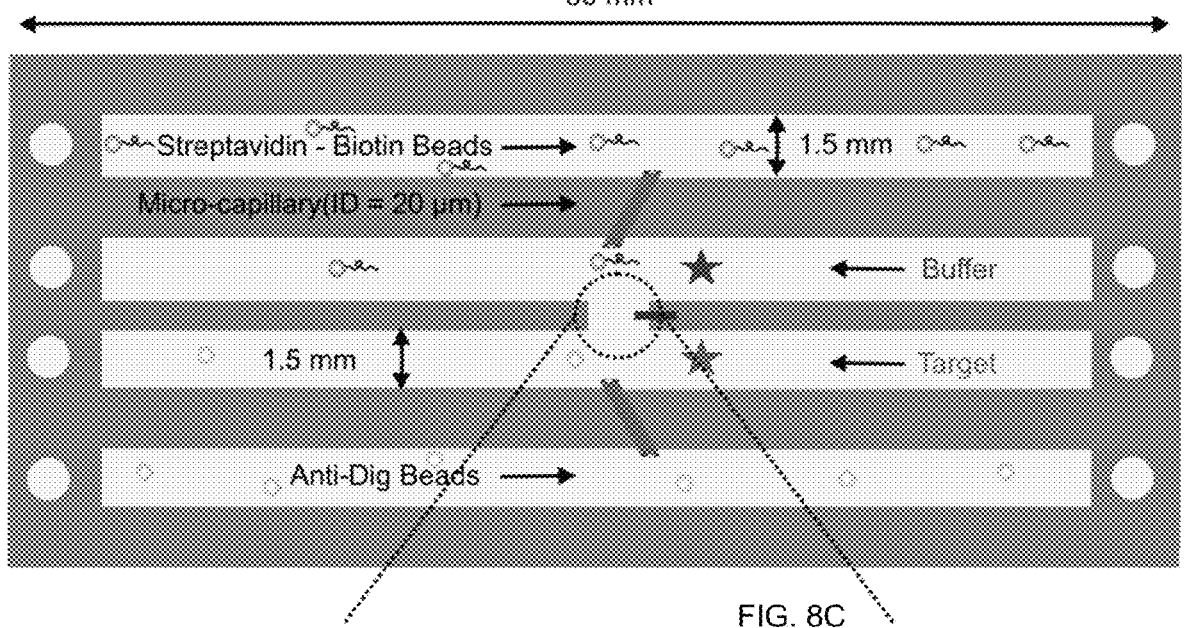
FIG. 8A shows a four channel microfluidic chamber.
Figure 8B:
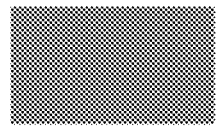
FIGS. 8B and 8C show a schematic of mechonochemical experiment.
Figure 8C:
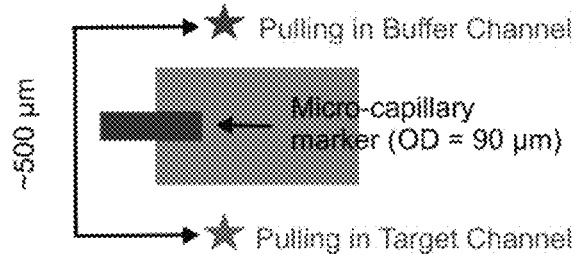

The single-molecule mechanochemical studies were performed in a microfluidic channel within laser tweezers instrument. The microfluidic patterns (FIG. 8) were prepared by Corel Draw program (Corel Corporation, Ottawa, Canada) and imprinted into the Para-film (BEMIS, Neenah, Wis.) on a glass cover slip by a laser cutter (VL-200, Universal Laser Systems, Scottsdale, Ariz.). The imprinted Nesco-film was thermally sealed at 85° C. between two #1 VWR cover glass slips. Two microcapillary tubes (ID 20 µm, OD 90 µm) were used to transport streptavidin- and anti-digoxigenin-antibody-coated beads into the buffer and target channels, respectively. The same type of the tube was used as a separation marker in the conduit between the two channels. The distance between the buffer and the target channels through the conduit is ~500 µm (see inset of FIG. 8). The pulling positions in the buffer and the target channels were kept in the middle of the channel to avoid the variation of flow rates from the edge effects.

Detailed description of the laser tweezers instrument has been reported elsewhere[27]. In brief, a diode pumped solid-state laser source (DPSS, 1,064 nm wavelengths in continuous-wave mode, BL-106C, Spectra-physics) was used to generate P- and S-polarized laser beams for two laser traps. The position of each trap was detected separately using two position-sensitive photo detectors (DL100, Pacific Silicon Sensor). A steerable mirror (Nano-MTA, Mad City Laboratories) was used to control the S-polarized light at the plane conjugate to the back focal plane of a focusing objective (Nikon CFI-Plan-Apochromat ×60, NA=1.2, water immersion, working distance ~320 µm). During the experiments, the tension inside the DNA construct was varied by the movement of the steerable mirror using the LabView 8 program (National Instruments Corporation).

To start the sensing experiments, the DNA construct was first immobilized onto the surface of the anti-digoxigenin antibody-coated polystyrene beads (diameter: 2.10 µm) through the antibody-antigen complex formation. The incubated sample was further diluted to 1 mL in a 10 mM Tris buffer with 100 mM KCl (pH 7.4). The streptavidin coated polystyrene beads (diameter: 1.87 µm) were also dispersed into the same buffer and injected into the microfluidic chamber. A 10 mM Tris buffer containing 100 mM KCl and 5 mM EDTA without $Hg^{2+}$ was flowed in the top (buffer) channel. The same buffer containing $Hg^{2+}$ without EDTA was injected in the bottom (target) channel. Two separate laser beams were used to trap two different types of beads (see above). By escorting one of the trapped beads closer to another using the steerable mirror, the DNA was tethered between the two trapped beads in the buffer channel. After the tethering, one of the trapped beads was moved away from another with a loading speed of ~5.5 pN/s. This rate allowed us to collect significant amount of data in a reasonable timescale at a condition close to the unfolding equilibrium of a free DNA hairpin. An unfolding event was identified as a sudden change in the end-to-end distance during the force ramping. The unfolding force was measured directly from the F-X curves while the change-in-contour-length (ΔL) due to the unfolding was calculated by the data points flanking the rupture event using an extensible worm-like chain (WLC) model (Equation 1)[28,29].

$$\frac{\Delta x}{\Delta L} = 1 - \frac{1}{2}\left(\frac{k_B T}{FP}\right)^{\frac{1}{2}} + \frac{F}{S} \quad (1)$$

where Δx is the change in extension between the data points of the stretching and relaxing curves at the same force (F), $k_B$ is the Boltzmann constant, T is absolute temperature, P is the persistent length (50.8±1.5 nm)[30], and S is the elastic stretch modulus (1243±63 pN)[30]. The stochastic bi-state transition (or mechanoescence) of the hairpin was observed with a fixed tension in the DNA template (see FIG. 3). ΔL was calculated using the following equation (Equation 2), $$\Delta L = L - \Delta x = N \times L_{nt} - \Delta x \quad (2)$$

where N is the number of nucleotides contained in the structure, $L_{nt}$ is the contour length per nucleotide (~0.45 nm)[31], and Ax is the end-to-end distance (~2 nm, the diameter dsDNA)[32].

While in accordance with the patent statutes, the best mode and preferred embodiment have been set forth, the scope of the invention is not limited thereto, but rather by the scope of the attached claims.

REFERENCES

1. Cammann, K. Bio-sensors based on ion-selective electrodes. *Anal. Chem.* 287, 1-9 (1977).
2. Thevenot, D. R., Toth, K., Durst, R. A. & Wilson, G. S. *Electrochemical biosensors: recommended definitions and classification, Biosens. Bioelectron.* 16(1-2), 121-31, (2001).
3. Anthony, T., George, W. & Isao, K. *Biosensors: Fundamentals and Applications*, Oxford University Press, Oxford, UK, 1987.
4. Lequin, R. M. Enzyme immunoassay (EIA)/enzyme-linked immunosorbent assay (ELISA). *Clin. Chem.* 51, 2415-2418 (2005).
5. Shrestha, P., Mandal, S. & Mao, H. Mechanochemical Sensing: A Biomimetic Sensing Strategy. *ChemPhysChem* 16, 1829-1837 (2015).
6. Tchounwou, P. B., Ayensu, W. K., Ninashvili, N. & Sutton, D. Review: Environmental exposure to mercury and its toxicopathologic implications for public health. *Environ. Toxicol.* 18, 149-175 (2003).

7. Miyake, Y. et al. MercuryII-Mediated Formation of Thymine-Hg(II)-Thymine Base Pairs in DNA Duplexes. *J. Am. Chem. Soc.* 128, 2172-2173 (2006).
8. Cizdziel, J. V. & Gerstenberger, S. Determination of total mercury in human hair and animal fur by combustion atomic absorption spectrometry. *Talanta* 64, 918-921 (2004).
9. Suvarapu, L. N. & Baek, S. O. Recent Developments in the Speciation and Determination of Mercury Using Various Analytical Techniques. *J. Anal. Methods Chem.* 372459, 5 (2015).
10. U.S. EPA. National Primary Drinking Water Regulations. US EPA, 2009. http://water.epa.gov/drink/contaminants/index.cfm#List.
11. Jenner, G. A., Longerich, H. P., Jackson, S. E. & Fryer, B. J. ICP-MS—A powerful tool for high-precision trace-element analysis in Earth sciences: Evidence from analysis of selected U.S.G.S. reference samples. *Chem. Geol.* 83, 133-148 (1990).
12. Li, Y. & Hu, B. Sequential cloud point extraction for the speciation of mercury in seafood by inductively coupled plasma optical emission spectrometry. *Spectrochim. Acta B* 62, 1153-1160 (2007).
13. Ghaedi, M., Reza Fathi, M., Shokrollahi, A. & Shajarat, F. Highly selective and sensitive preconcentration of mercury ion and determination by cold vapor atomic absorption spectroscopy. *Anal. Lett.* 39, 1171-1185 (2006).
14. Oliveira, E. d. Sample preparation for atomic spectroscopy: evolution and future trends. *J. Braz. Chem. Soc.* 14, 174-182 (2003).
15. Kong, R.-M. et al. An ultrasensitive electrochemical "turn-on" label-free biosensor for Hg2+ with AuNP-functionalized reporter DNA as a signal amplifier. *Chem. Commun.*, 5633-5635 (2009).
16. Yang, H. et al. Multisignaling Optical-Electrochemical Sensor for $Hg^{2+}$ Based on a Rhodamine Derivative with a Ferrocene Unit. *Org. Lett.* 9, 4729-4732 (2007).
17. Jiang, Z. et al. Resonance Scattering Spectral Detection of Trace $Hg^{2+}$ Using Aptamer-Modified Nanogold as Probe and Nanocatalyst. *Anal. Chem.* 81, 5439-5445 (2009).
18. Nolan, E. M., Racine, M. E. & Lippard, S. J. Selective Hg(II) Detection in Aqueous Solution with Thiol Derivatized Fluoresceins. *Inorg. chem.* 45, 2742-2749 (2006).
19. Yang, Y.-K., Yook, K.-J. & Tae, J. A Rhodamine-Based Fluorescent and Colorimetric Chemodosimeter for the Rapid Detection of $Hg^{2+}$ Ions in Aqueous Media. *J. Am. Chem. Soc.* 127, 16760-16761 (2005).
20. Liu, M., Zhang, W., Zhang, Q., Brennan, J. D. & Li, Y. Biosensing by Tandem Reactions of Structure Switching, Nucleolytic Digestion, and DNA Amplification of a DNA Assembly. *Angew. Chem. Int. Ed.* 54, 9637-9641 (2015).
21. Zhang, S., Garcia-D'Angeli, A., Brennan, J. P. & Huo, Q. Predicting detection limits of enzyme-linked immunosorbent assay (ELISA) and bioanalytical techniques in general. *Analyst* 139, 439-445 (2014).
22. Mandal, S., Koirala, D., Selvam, S., Ghimire, C. & Mao, H. A Molecular Tuning Fork in Single-Molecule Mechanochemical Sensing. *Angew. Chem. Int. Ed.* 54, 7607-7611 (2015).
23. Woodside, M. T. et al. Nanomechanical measurements of the sequence-dependent folding landscapes of single nucleic acid hairpins. *Proc. Natl. Acad. Sci. USA.* 103, 6190-6195 (2006).
24. Torigoe, H., Ono, A. & Kozasa, T. Hg(II) ion specifically binds with T:T mismatched base pair in duplex DNA. *Chemistry* 16, 13218-25 (2010).
25. Mammen, M., Choi, S.-K. & Whitesides, G. M. Polyvalent interactions in biological systems: implications for design and use of multivalent ligands and inhibitors. *Angew. Chem. Int. Ed.* 37, 2754-2794 (1998).
26. Koirala, D. et al. Single-molecule mechanochemical sensing using DNA origami nanostructures. *Angew. Chem. Int. Ed.* 53, 8137-8141 (2014).
27. Mao, H. & Luchette, P. An integrated laser-tweezers instrument for microanalysis of individual protein aggregates. *Sens. Actuators B* 129, 764-771 (2008).
28. Baumann, C. G., Smith, S. B., Bloomfield, V. A. & Bustamante, C. Ionic effects on the elasticity of single DNA molecules. *Proc. Natl. Acad. Sci. USA* 94, 6185-6190 (1997).
29. Yu, Z. & Mao, H. Non-B DNA structures show diverse conformations and complex transition kinetics comparable to RNA or proteins—a perspective from mechanical unfolding and refolding experiments. *Chem. Rec.* 13, 102-116 (2013).
30. Dhakal, S. et al. Structural and mechanical properties of individual human telomeric G-quadruplexes in molecularly crowded solutions. *Nucleic Acids Res.* 41, 3915-3923 (2013).
31. Mills, J. B., Vacano, E. & Hagerman, P. J. Flexibility of single-stranded DNA: use of gapped duplex helices to determine the persistence lengths of poly(dT) and poly (dA). *J. Mol. Biol.* 285, 245-257 (1999).
32. R. R. Sinden, DNA Structure and Function., Academic Press, San Diego, Calif., 1995.

What is claimed is:

1. A single-molecule mechanoanalytical real-time sensing device (SMART) comprising:
   - a molecular trawl and a DNA stem-loop structure that serves as a molecular dipstick, said trawl and said DNA stem-loop structure capable of being anchored by handles to two optically-trapped beads;
   - said molecular trawl comprising multiple analyte recognition elements that exist in each of two separate DNA strands that act as two pincers, said pincers each having an analyte recognition element capable of catching an analyte in a media;
   - said DNA stem-loop structure comprising a plurality of nucleotides and multiple base pairs;
   - wherein said DNA stem-loop is located generally opposite to said molecular trawl that is capable of reporting an amount of bound analyte target via mechanochemical transient events; and
   - wherein said bound analyte target is $Hg^{2+}$.

2. The SMART device of claim 1, wherein said anchoring beads are essentially at a standstill and wherein a fluid is forced through said mechanoanalytical device, and wherein said trawl and said stem-loop structures are anchored to said optical-trapped beads by two dsDNA handle strands.

3. The SMART device of claim 1, wherein each said two separate DNA trawl strands, independently, comprise one or more of an adenine (A), cytosine (C), guanine (G), or thymine (T) nucleotide or any combination thereof, wherein each said two separate trawl DNA strands, independently, contain from 2 to about 200 nucleotides therein; wherein each said two separate trawl DNA strand contains a specific antigen element that is capable of recognizing a specific analyte; wherein said loop nucleotides comprise one or more adenine, cytosine, guanine, or thymine, or any combination thereof, and wherein said stem base pairs nucleotides, independently, comprise one or more of adenine, cytosine, guanine, or thymine, or any combination thereof, and wherein said loop nucleotides are the same or different from said stem nucleotides.

4. The SMART device of claim 3, wherein said analyte recognition element comprises a protein, or one or more nucleic acids or a separate sequence, in each said two separate DNA strands; wherein said loop (single stranded DNA) has from about 2 to about 20 nucleotides, and wherein said stem (double stranded DNA) has from about 8 to about 40 or about 60 total base pairs; and wherein each handle (double stranded DNA), independently, has from about 2,000 to about 4,000 base-pairs.

5. The SMART device of claim 4, wherein each said DNA trawl strand, independently, contains from about 10 to about 100 nucleotides, wherein said loop (single stranded DNA) has from about 2 to about 10 nucleotides, and wherein said stem (double stranded DNA) has from about 10 to about 25 total base pairs; wherein each handle (double stranded DNA), independently, has from about 2,000 to about 2,500 base-pairs.

6. The SMART device of claim 5, wherein said analyte recognition element comprises polythymine DNA strands, polycytosine DNA strands, B-DNA strands, or two separate DNA strands (ssDNA) labeled with a specific antigen.

7. The SMART device of claim 6, wherein each said DNA trawl strand, independently, contains from about 20 to about 50 nucleotides, wherein said loop (single stranded DNA) has from about 2 to about 6 nucleotides, and wherein said stem (double stranded DNA) has from about 15 to about 20 total base pairs.

8. The SMART device of claim 3, wherein said optically-trapped bead comprises glass, fused silica, boron nitride, a polymer, or any combination thereof; wherein said bead is optically-trapped by a laser, and wherein a force to unzip said stem-loop structure is from about 8 to about 20 pN.

9. The SMART device of claim 4, wherein said optical bead comprises a polymer; wherein said bead is optically-trapped by a laser, and wherein a force to unzip said stem-loop structure is from about 8 to about 20 pN.

10. The SMART device of claim 7, wherein said optical bead comprises a polymer; wherein said bead is optically-trapped by a laser, and wherein a force to unzip said stem-loop structure is from about 8 to about 20 pN.

11. The SMART device of claim 3, wherein said analyte comprises ATP; cocaine; melamine; a nucleic acid; an antibody; a bacteria; a toxic metal; or a disease biomarker; and any combination thereof.

12. The SMART device of claim 5, wherein said analyte comprises ATP; cocaine; melamine; a nucleic acid; an antibody; a bacteria; a toxic metal; or a disease biomarker; and any combination thereof.

13. The SMART device of claim 7, wherein said analyte comprises ATP; cocaine; melamine; a nucleic acid; an antibody; a bacteria comprising a *Mycobacterium ulceran*, or a *Bordetella avium*; a toxic metal comprising Pb, Ag, or As, or a disease biomarker comprising a HIV-1 protease, or hepatitis C virus helicase; or any combinations thereof.

14. The SMART device of claim 1, wherein said device is located in a media, and wherein the index of refraction of said bead is greater than the index of refraction of said media.

15. The SMART device of claim 3, wherein said device is located in a media, and wherein the index of refraction of said bead is greater than the index of refraction of said media.

16. The SMART device of claim 7, wherein said device is located in a media, wherein said media is water for an aqueous buffer system, and wherein the index of refraction of said bead is greater than the index of refraction of said media.

17. A process for measuring very small amounts of an analyte according to claim 1, comprising the steps of:
    forming a SMART device, said SMART device comprising:
    a molecular trawl and a DNA stem-loop structure that serves as a molecular dipstick, said trawl and said DNA stem-loop structure anchored by handles to two optically-trapped beads;
    said molecular trawl comprising multiple analyte recognition elements that exist in each of two separate DNA strands that act as two pincers, said pincers each having an analyte recognition element capable of catching an analyte in a media;
    said DNA stem-loop structure comprising a plurality of nucleotides and multiple base pairs; and
    wherein said DNA stem-loop is located generally opposite to said molecular trawl that is capable of reporting an amount of bound analyte target via mechanochemical transient events; and
    calculating the amount of analyte captured by said SMART device.

18. The process of claim 17, wherein each said two separate DNA trawl strands, independently, comprise one or more of an adenine (A), cytosine (C), guanine (G), or thymine (T) nucleotide or any combination thereof, wherein each said two separate trawl DNA strands, independently, contain from 2 to about 200 nucleotides therein; wherein each said two separate trawl DNA strand contains a specific antigen element that is capable of recognizing a specific analyte; wherein said loop nucleotides comprise one or more adenine, cytosine, guanine, or thymine, or any combination thereof, and wherein said stem base pairs nucleotides, independently, comprise one or more of adenine, cytosine, guanine, or thymine, or any combination thereof, and wherein said loop nucleotides are the same or different from said stern nucleotides.

19. The process of claim 18, wherein said analyte recognition element comprises a protein, or one or more nucleic acids, or a separate sequence, in each said two separate DNA strands; wherein said loop (single stranded DNA) has from about 2 to about 20 nucleotides, and wherein said stem (double stranded DNA) has from about 8 to about 40 or about 60 total base pairs; and wherein each handle (double stranded DNA), independently, has from about 2,000 to about 4,000 base-pairs.

20. The process of claim 19, wherein each said DNA trawl strand, independently, contains from about 10 to about 100 nucleotides, wherein said loop (single stranded DNA) has from about 2 to about 10 nucleotides, and wherein said stem (double stranded DNA) has from about 10 to about 25 total base pairs; wherein each handle (double stranded DNA), independently, has from about 2,000 to about 2,500 basepairs.

* * * * *

SEQUENCE LISTING

<160> NUMBER OF SEQ ID NOS: 19

<210> SEQ ID NO 1
<211> LENGTH: 35
<212> TYPE: DNA
<213> ORGANISM: Artificial Sequence
<220> FEATURE:
<223> OTHER INFORMATION: Oligonucleotides

<400> SEQUENCE: 1
ctagtgcatt aggaacgagc ccagaaaggt gcacc                                35

<210> SEQ ID NO 2
<211> LENGTH: 23

```
<212> TYPE: DNA
<213> ORGANISM: Artificial Sequence
<220> FEATURE:
<223> OTHER INFORMATION: Oligonucleotides

<400> SEQUENCE: 2
gtccggaccc tgtttcaggg tcc                                        23

<210> SEQ ID NO 3
<211> LENGTH: 36
<212> TYPE: DNA
<213> ORGANISM: Artificial Sequence
<220> FEATURE:
<223> OTHER INFORMATION: Oligonucleotides

<400> SEQUENCE: 3
ggacggtgca ccaaaagcaa gacgtagccc agcgcg                          36

<210> SEQ ID NO 4
<211> LENGTH: 29
<212> TYPE: DNA
<213> ORGANISM: Artificial Sequence
<220> FEATURE:
<223> OTHER INFORMATION: Oligonucleotides

<400> SEQUENCE: 4
ggcccgcgct gggctacgtc ttgcttttt                                  29

<210> SEQ ID NO 5
<211> LENGTH: 24
<212> TYPE: DNA
<213> ORGANISM: Artificial Sequence
<220> FEATURE:
<223> OTHER INFORMATION: Oligonucleotides

<400> SEQUENCE: 5
ttttctgggc tgcttcctaa tgca                                       24

<210> SEQ ID NO 6
<211> LENGTH: 29
<212> TYPE: DNA
<213> ORGANISM: Artificial Sequence
<220> FEATURE:
<223> OTHER INFORMATION: Oligonucleotides

<400> SEQUENCE: 6
ggcccgcgct gggctacgtc ttgctcttt                                  29

<210> SEQ ID NO 7
<211> LENGTH: 24
<212> TYPE: DNA
<213> ORGANISM: Artificial Sequence
<220> FEATURE:
<223> OTHER INFORMATION: Oligonucleotides

<400> SEQUENCE: 7
ttagctgggc tgcttcctaa tgca                                       24

<210> SEQ ID NO 8
<211> LENGTH: 35
<212> TYPE: DNA
<213> ORGANISM: Artificial Sequence
<220> FEATURE:
<223> OTHER INFORMATION: Oligonucleotides

<400> SEQUENCE: 8
```

```
ggcccgcgct gggctacgtc ttgctctttg tgttc                          35
```

<210> SEQ ID NO 9
<211> LENGTH: 30
<212> TYPE: DNA
<213> ORGANISM: Artificial Sequence
<220> FEATURE:
<223> OTHER INFORMATION: Oligonucleotides

<400> SEQUENCE: 9

```
gttcacttag ctgggctgct tcctaatgca                                30
```

<210> SEQ ID NO 10
<211> LENGTH: 37
<212> TYPE: DNA
<213> ORGANISM: Artificial Sequence
<220> FEATURE:
<223> OTHER INFORMATION: Oligonucleotides

<400> SEQUENCE: 10

```
ggcccgcgct gggctacgtc ttgctctttt ttttttt                        37
```

<210> SEQ ID NO 11
<211> LENGTH: 32
<212> TYPE: DNA
<213> ORGANISM: Artificial Sequence
<220> FEATURE:
<223> OTHER INFORMATION: Oligonucleotides

<400> SEQUENCE: 11

```
tttttttttt agctgggctg cttcctaatg ca                             32
```

<210> SEQ ID NO 12
<211> LENGTH: 77
<212> TYPE: DNA
<213> ORGANISM: Artificial Sequence
<220> FEATURE:
<223> OTHER INFORMATION: Oligonucleotides

<400> SEQUENCE: 12

```
ggcccgcgct gggctacgtc ttgctctttt tttttttttt tttttttttt tttttttttt  60
tttttttttt ttttttt                                               77
```

<210> SEQ ID NO 13
<211> LENGTH: 72
<212> TYPE: DNA
<213> ORGANISM: Artificial Sequence
<220> FEATURE:
<223> OTHER INFORMATION: Oligonucleotides

<400> SEQUENCE: 13

```
tttttttttt tttttttttt tttttttttt tttttttttt tttttttttt agctgggctg  60
cttcctaatg ca                                                    72
```

<210> SEQ ID NO 14
<211> LENGTH: 67
<212> TYPE: DNA
<213> ORGANISM: Artificial Sequence
<220> FEATURE:
<223> OTHER INFORMATION: Oligonucleotides

<400> SEQUENCE: 14

```
ctagtgcatt aggaacgagc ccagaaagat cagtagcgag ctgcagtgt acggaggtcg   60 gtgcatc                                                          67
```

```
<210> SEQ ID NO 15
<211> LENGTH: 24
<212> TYPE: DNA
<213> ORGANISM: Artificial Sequence
<220> FEATURE:
<223> OTHER INFORMATION: Oligonucleotides

<400> SEQUENCE: 15
gtccggaccc tgttttcagg gtcc                                           24

<210> SEQ ID NO 16
<211> LENGTH: 68
<212> TYPE: DNA
<213> ORGANISM: Artificial Sequence
<220> FEATURE:
<223> OTHER INFORMATION: Oligonucleotides

<400> SEQUENCE: 16
ggacgatgca ccgacctccg tacactgcag cctcgctact gatcaaaagc aagacgtagc    60
ccagcgcg                                                             68

<210> SEQ ID NO 17
<211> LENGTH: 89
<212> TYPE: DNA
<213> ORGANISM: Artificial Sequence
<220> FEATURE:
<223> OTHER INFORMATION: Oligonucleotides

<400> SEQUENCE: 17
ctagtgcatt aggaagcagc ccagaaagca ggaacaggga atgcccgttt tcgggcattc    60
cctgttcctg cctatctaac tggtgcacc                                      89

<210> SEQ ID NO 18
<211> LENGTH: 24
<212> TYPE: DNA
<213> ORGANISM: Artificial Sequence
<220> FEATURE:
<223> OTHER INFORMATION: Oligonucleotides

<400> SEQUENCE: 18
gtccggaccc tgttttcagg gtcc                                           24

<210> SEQ ID NO 19
<211> LENGTH: 36
<212> TYPE: DNA
<213> ORGANISM: Artificial Sequence
<220> FEATURE:
<223> OTHER INFORMATION: Oligonucleotides

<400> SEQUENCE: 19
ggacggtgca ccaaaagcaa gacgtagccc agcgcg                              36
```